(12) United States Patent
Buch et al.

(10) Patent No.: US 7,047,252 B2
(45) Date of Patent: May 16, 2006

(54) COMPLEX COMPUTATION ACROSS HETEROGENOUS COMPUTER SYSTEMS

(75) Inventors: Vineet Buch, Foster City, CA (US); Sashikanth Chandrasekaran, Belmont, CA (US)

(73) Assignee: Oracle International Corporation, Redwood Shores, CA (US)

( * ) Notice: Subject to any disclaimer, the term of this patent is extended or adjusted under 35 U.S.C. 154(b) by 101 days.

(21) Appl. No.: 10/724,834

(22) Filed: Dec. 2, 2003

(65) Prior Publication Data
US 2005/0119988 A1    Jun. 2, 2005

(51) Int. Cl.
*G06F 17/30* (2006.01)
(52) U.S. Cl. .................. 707/102; 707/103 R
(58) Field of Classification Search ........... 707/1–10, 707/100–104.1; 709/201–203; 345/419; 370/466
See application file for complete search history.

(56) References Cited

U.S. PATENT DOCUMENTS

| | | | |
|---|---|---|---|
| 6,009,455 A | | 12/1999 | Doyle |
| 6,041,344 A | | 3/2000 | Bodamer et al. |
| 6,434,594 B1 | | 8/2002 | Wesemann |
| 6,483,851 B1 | * | 11/2002 | Neogi .................. 370/466 |
| 2003/0158886 A1 | * | 8/2003 | Walls et al. ............ 709/201 |
| 2003/0160780 A1 | * | 8/2003 | Lefebvre et al. ........ 345/419 |
| 2003/0212742 A1 | * | 11/2003 | Hochmuth et al. ...... 709/204 |

OTHER PUBLICATIONS

Patent Cooperation Treaty, "International Search Report," PCT/US2004040114, dated Apr. 20, 2005, 8 pages.
Current Claims, PCT/US2004040114, 3 pages.

* cited by examiner

*Primary Examiner*—Diane D. Mizrahi
(74) *Attorney, Agent, or Firm*—Hickman Palermo Truong & Becker, LLP; Christopher J. Brokaw

(57) ABSTRACT

A programmatic interface to allow external functions to be registered and called in parallel from within a database management system is described for coordinating a computation at multiple nodes. In one embodiment, each node executes a process configured for starting a program to perform the computation in response to a command received from a database system. In response to receiving a query at the database system, multiple commands are transmitted to the processes for concurrently performing the computation at each said corresponding process. Results are received from each of the processes and execution of the statement is completed based on the results received.

17 Claims, 3 Drawing Sheets

COMPLEX COMPUTATION ACROSS HETEROGENOUS COMPUTER SYSTEMS

FIELD OF THE INVENTION

The present invention relates to database systems and more particularly to complex computation across heterogeneous computer systems.

BACKGROUND OF THE INVENTION

A common scenario in scientific computing is to run a complex computation across multiple heterogeneous environments, accessing and processing data stored in a variety of different formats. For example, one complex computation is to search for a DNA match of genetic material within various databases of genetic sequences and their citations. Heterogeneous environments contain different, and often incompatible, combinations of hardware, operating system, and application software. Typically, these different systems are purchased independently to serve a particular need, and enterprises may have information spread across multiple computer systems. Since system vendors attempt to provide a competitive edge over the offerings of their competitors, the different systems are almost by definition incompatible. Even relational database management systems (DBMS) based on the Structured Query Language (SQL) standards and the relational model can be incompatible due to differences in SQL implementations, database definition, and communication mechanisms. Hence, the task of combining heterogeneous systems for executing complex computations is difficult.

In executing complex computations over multiple, heterogeneous environments, a database management system is often used as the ultimate repository of the results of the computation, as well as the source of some of the data used in the computation. However, integrating yet another heterogeneous system, i.e., the database management system, into the environment presents additional complications to the already difficult task of executing the complex computation.

For example, one approach for managing such complex computations is known as multi-stage processing, in which the complex computation is broken up into multiple steps, each step submitted by the user and taking place in its entirety and independently on a homogeneous platform. Results of each computation are combined in a separate step and loaded into the results database. The coordination of the computation steps is either done manually or using some form of a workflow engine, and the complete computational results are only available after being executed in batch mode, not interactively. Thus, in the multi-stage processing approach, integration with the database system is poor and non-interactive, essentially reducing the database system to an after-the-fact user interface to results of previously executed runs of data. Furthermore, coordination of the execution the computations is difficult to achieve in a robust and scalable manner.

A more interactive approach is to code the specific coordination steps in a database query that can be submitted by a user. When the user submits the specifically coded query to the database system, the query is executed, causing the database system to initiate the various sub-components of the complex computation and combine the results together. Coding the query in this approach requires that the developer have an intimate knowledge of each heterogeneous system, the parts of the computation are to be executed upon and manage the execution of the parts outside the database. This approach is not general in scope and only addresses a specific computation.

Another approach is to leverage the parallel query, clustering, and two-phase commit mechanisms of some database systems that allow a single query to be executed across multiple (homogeneous) database instances. In this approach, the data present on an incompatible system is migrated into one or more of the database and the algorithms used to perform the computation are rewritten to function within the database. However, this migrate-and-rewrite approach is expensive and time-consuming and requires investment in hardware so that each node is capable of executing a database instance, database management system software as well as database administration and application development resources. In addition, it may not be feasible to rewrite the algorithms to be executed in the database.

Therefore, there is a need for a robust, scalable, interactive, and inexpensive approach for performing complex computation across multiple heterogeneous database systems.

SUMMARY OF THE INVENTION

These and other needs are addressed by the present invention, a programmatic interface that allows external functions to be registered and called in parallel from within a database management system. Accordingly, one aspect of the invention relates to a method for coordinating a computation at multiple nodes, each executing a process configured for starting a program to perform the computation in response to a command received from a database system. In response to receiving a query at the database system, multiple commands are transmitted to the processes for concurrently performing the computation to each said corresponding process. Results are received from each of the processes and execution of the statement is completed based on the results received.

Another aspect of the present invention is directed to a method and software for coordinating a computation upon multiple data containers deployed at multiple nodes. In response to receiving a statement or query at a database system specifying an external routine for performing the computation, commands for performing the computation are transmitted to a process configured for starting programs to perform the computation. Results are received from each of the processes and execution of the statement is completed based on the results received. In one embodiment, a cohort of the nodes for performing the computation is determined based on various criteria, such as the degree of parallelism and the number of available threads.

Still other aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various obvious respects, all without departing from the spirit and scope of the present invention. Accordingly, the drawing and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF THE PREFERRED EMBODIMENT

A system, method, and software for complex computation are described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention.

In a database management system, data is stored in one or more data containers, each container contains records, and the data within each record is organized into one or more fields. In relational database systems, the data containers are referred to as tables, the records are referred to as rows, and the fields are referred to as columns. In object-oriented databases, the data containers are referred to as object classes, the records are referred to as objects and the fields are referred to as attributes. Other database architectures may use other terminology.

Systems that implement the present invention are not limited to any particular type of data container or database architecture. However, for the purpose of explanation, the terminology and examples used herein shall be that typically associated with relational databases. Thus, the terms "table," "row," and "column" shall be used herein to refer respectively to the data container, record, and field.

System Overview

Figure 1:
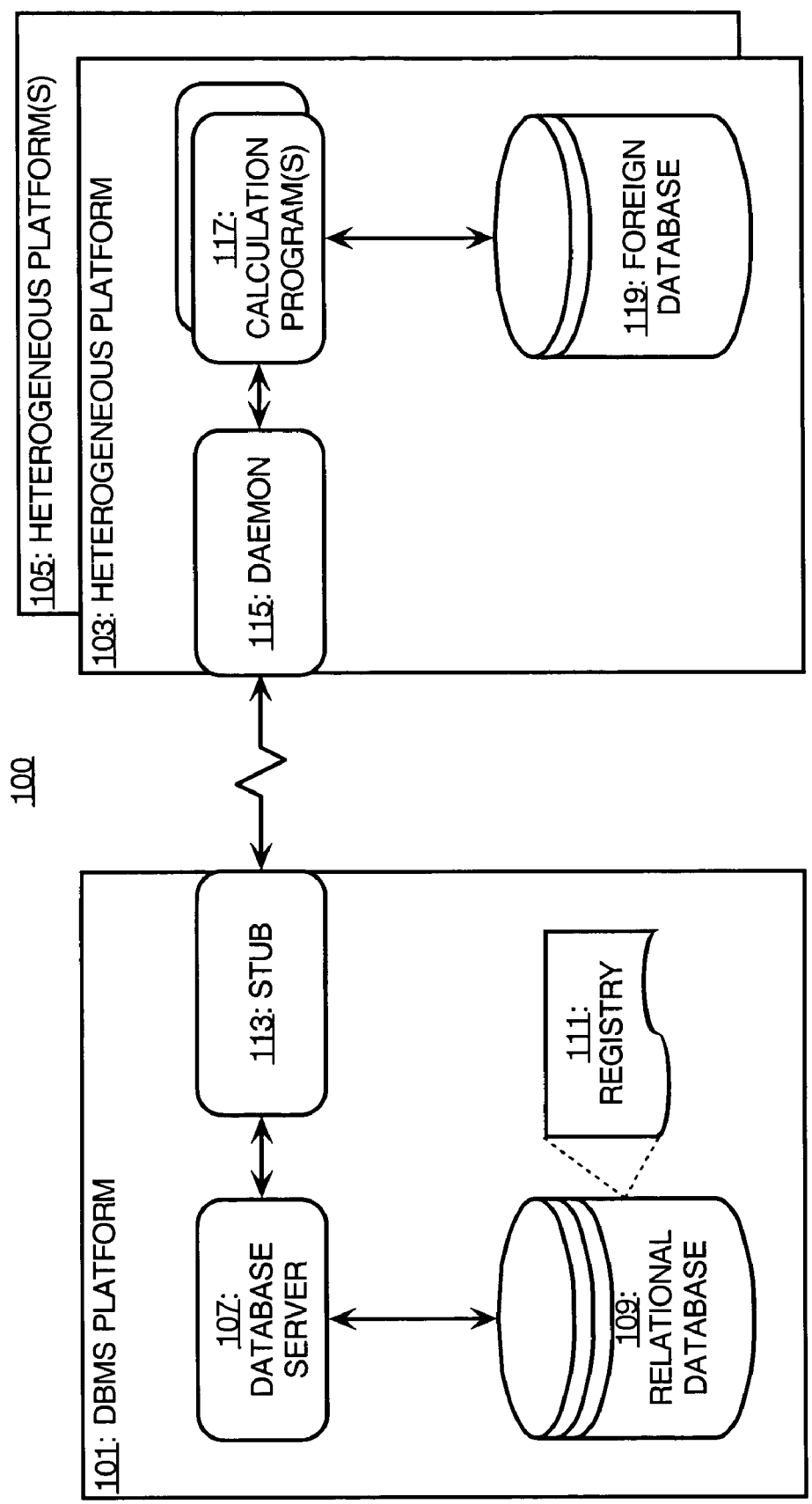
FIG. 1 depicts a heterogeneous environment that can be used in deploying an embodiment of the present invention.

FIG. 1 is a schematic diagram of a heterogeneous environment 100 in which an embodiment of the present invention can be deployed to perform a complex calculation. Specially, the heterogeneous environment 100 includes a database management system (DBMS) platform 101 and a heterogeneous platform 103. Platform 103 can be considered heterogeneous if the combination of hardware, operating system, and application software differs from or is incompatible with the hardware, operating system, and application software on the DBMS platform 101. Depending on the deployment environment, embodiments of the present invention may include one or more additional heterogeneous platforms 105. Even though the platforms 103 and 105 are described as heterogeneous herein, one of more of the platforms 103 and 105 can be homogeneous with that of the DBMS platform 101 and still attain some of the benefits derived from other aspects of the present invention. Thus, the present invention can be advantageous in homogeneous or mixed homogeneous/heterogeneous environments.

DBMS platform 101 provides an interface to a user or application program for performing a complex calculation across multiple heterogeneous platforms 103 and 105, coordinates the complex calculation among the heterogeneous platforms 103 and 105, and serves as a repository of the results of the complex calculation from the heterogeneous platforms 103 and 105. In one embodiment, the DBMS platform 101 includes a database server 107 for receiving a query from the user or application program specifying the complex calculation, a relational database 109 for storing the results of the complex calculation as well as other data that participates in the complex calculation, a programming interface registry 111 for coordinating the distributed complex calculation, and a stub program 113 generated by the programming interface based on the information in the programming interface registry 111. The programming interface registry 111 and the stub program 113 are described in greater detail below.

The stub program 113 is configured to open a network connection or other communications link to a daemon 115 executing on the heterogeneous platform 103 as well as corresponding daemons (not shown) executing on the heterogeneous platforms 105. Without loss of generality and for convenience of description, the system architecture of the heterogeneous platforms 103 and 105 is described solely with respect to heterogeneous platform 103. The daemon 115 is a preferably a background process that continuously idles until activated by a communication from the stub program 113. When activated, the daemon 115 is configured to start, pass arguments to, and stop execution of one or more calculation programs 117. The one or more calculation programs 117 may interact with a foreign database 119 for performing a complex computation and return results ultimately to the database server 107 for storage in the relational database 109 and presentation to the user or application program.

Preferably, the stub program 113 and the daemon(s) 115 are configured to initiate the one or more calculation programs 117 on the one or more heterogeneous platforms 103 and 105 concurrently to achieve a degree of parallelism. In this configuration, the database server 107 commands a daemon 115 via the stub program 113 to start one or more calculation programs 117 with appropriate arguments, or pass arguments to an already running calculation program 117, or terminate an already running calculation program 117. The daemon 115 starts each requested calculation program 117 in turn in a non-blocking fashion and, after all the requested calculation programs 117 are started, waits for the calculation programs 117 to end. As each calculation program 117 ends, the results are returned to the requesting process in the DBMS platform 101. In one embodiment, the daemon 115 passes arguments to a running calculation program 117 in a non-blocking fashion, i.e., without waiting for results from the calculation program 117. The database server 107 can send a request to stop the execution of one or more of the calculation programs 117 running as part of an earlier request. After verifying that both requests originated from the same source, the daemon 115 may terminate the requested calculation programs 117.

Furthermore, each calculation program 117 registered with a daemon 115 may have a default degree of parallelism (e.g. number of concurrent threads of execution). This default can be over-ridden by a request from the database server 107 to start that calculation program 117 with a different number of threads. In this embodiment, each daemon 115 maintains a pool of available threads and tracks the status (busy, free) of each thread, starting a calculation program 117 by attaching the calculation program 117 to a thread and marking the thread as busy. If all threads in the pool are busy, new threads are created until the configurable threshold is reached. The daemon 115 will keeps the database server 107 updated on the status of its thread pool, e.g., number of total threads and number of busy threads, so that the database server 103 can manage the parallel invocation with other heterogeneous platforms 105.

Accordingly, a programmatic interface within the DBMS platform 101 is provided that allows a database query to make runtime calls to daemons 115 managing multiple and preferably parallel calculation programs 117 on each target heterogeneous platform 103 and 105. These daemons 115 manage the execution of non-database programs 117 on behalf of the database server 107. Both the programming interface that generates the stub program 113 and the daemons 117 that execute the calculation programs 117 can be made generic, so the application developer need not know the architecture of the distributed computer system 101 to write database queries for performing the complex calculation. Furthermore, setup of programming interface registry 117 that coordinates the complex calculation can be a one-time operation performed by the database administrator. As a result, a robust, scalable, and easy-to-use system for performing complex calculations across multiple heterogeneous computer systems is attained.

Programming Interface Registry

In one embodiment, applications running within the DBMS platform 101 can make calls to parallel programs 117 on other platforms 103 and 105 using a non-blocking programming interface that accesses the programming interface registry 111, which contains information that indicates the capabilities of the heterogeneous platforms 103 and 105 and the calculation programs 117 resident on the heterogeneous platforms 103 and 105 sufficient to coordinate the complex calculation among the heterogeneous platforms 103 and 105. This information is preferably entered previously by a database administrator but some of the information can be obtained interactively in the query. For example, information in the programming interface registry 111 can be used to identify available heterogeneous platforms 103 and 105 to the DBMS platform 101 and associate the calculation programs 117 with these platforms 103 and 105 for the programmatic interface in the database server 107 so that the database server can notify each daemon 115 of the programs 117 that can be run on the daemon's corresponding platform 103 and 105.

Registration data in the programming interface registry 111 may indicate: the name of the calculation programs 117, each computer 103 in the heterogeneous environment 100 that can run a respective calculation program 117, program arguments for invoking the calculation program 117 (number, data type, position), the data set that this calculation program 117 on this computer 103 can run on, and how the result of running the calculation program 117 is returned (usually, a collection of records). Other, more administrative type, information in the programming registry 111 may include: an indication whether the calculation program 117 need be restarted each time or can continue running and accept new arguments for each call; whether a partial result is allowed (a result may be considered partial if a proper subset of the computers 103 and 105 running a request for that calculation program 117 failed to return a valid result); and default and maximum degree of parallelism for the calculation program 117.

The programming interface registry 111 also includes data about each computer 103 within the heterogeneous environment 101. This information may include: the name of each computer 103 and 105, connectivity data for creating a communications link between the DBMS platform 101 and the heterogeneous platform 103 (IP address, authentication information); a timeout interval for acknowledgements from the heterogeneous platform 103; a number of retries after failure to receive an acknowledgement from the timeout interface; a heartbeat interval (amount of time between status messages from the daemon 115 on the computer) 103; and a number of missed heartbeats that, if met, signifies computer failure for the heterogeneous platform 103. In addition, parallel invocation can be further coordinated using thread pool status and maximum allowable size information in the programming interface registry 111.

Upon registration, a procedural stub 113 is generated for each calculation program 117 registered with programming interface registry 111, for example, by a programming interface program used to set up the programming interface registry 111. The stub program 113, coded in a programming language supported within the database server 103, provides a call interface to the calculation program 117. Parameters to the stub program 113 may include arguments for the calculation program 117, the data range to be operated on, and the desired degree of parallelism, as well as the return type (collection of database rows).

Accordingly, any program that can be executed as a function in a SQL query and return a set of results can be executed in parallel in the heterogeneous environment 100, which can be viewed as a compute cluster. If the result is defined as a set of rows, the function can be used in the FROM clause of a SQL query as a table function returning a set of rows. On the other hand, if the function does not return a set of rows (e.g., a collection of integers), that function could still be used in the SELECT list or user-defined methods for object types.

Table functions are functions that produce a collection of rows or a vector/array that can be queried like a physical database table or assigned to a PL/SQL collection variable. Syntactically, a table function can be used like the name of a database table in the FROM clause of a query or like a column name in the SELECT list of a query. A table function can take a collection of rows as input. Execution of a table function can be parallelized, and returned rows can be streamed directly to the next process without intermediate staging. In one implementation, rows from a collection returned by a table function can be pipelined or, in other words, iteratively returned as the rows are produced instead of all at once in a batch after completion of processing the table function's input. Thus, the streaming, pipelining, and parallel execution of table functions can improve performance by enabling multi-threaded, concurrent execution of table functions, by eliminating intermediate staging between processes, and by improving query response time. With non-pipelined table functions, the entire collection returned by a table function is constructed and returned to the server before the query can return a single result row. Pipelining enables rows to be returned iteratively, as they are produced. This also reduces the memory that a table function requires, as the object cache does not need to materialize the entire collection. By iteratively providing result rows from the collection returned by a table function as the rows are produced instead of waiting until the entire collection is staged in tables or memory and then returning the entire collection.

In one embodiment, for simplicity, functions that execute in the heterogeneous environment 101 are leaf-level functions and aggregations (MAX, MIN, DISTINCT, etc.) are performed by the database server 103. Depending on the aggregation, if any, to be performed by the database server 103, the rows that are pipelined from the calculation programs 117 may be returned immediately to the consumer row source or buffered for aggregation in the database server 107.

Operational Overview

Figure 2:
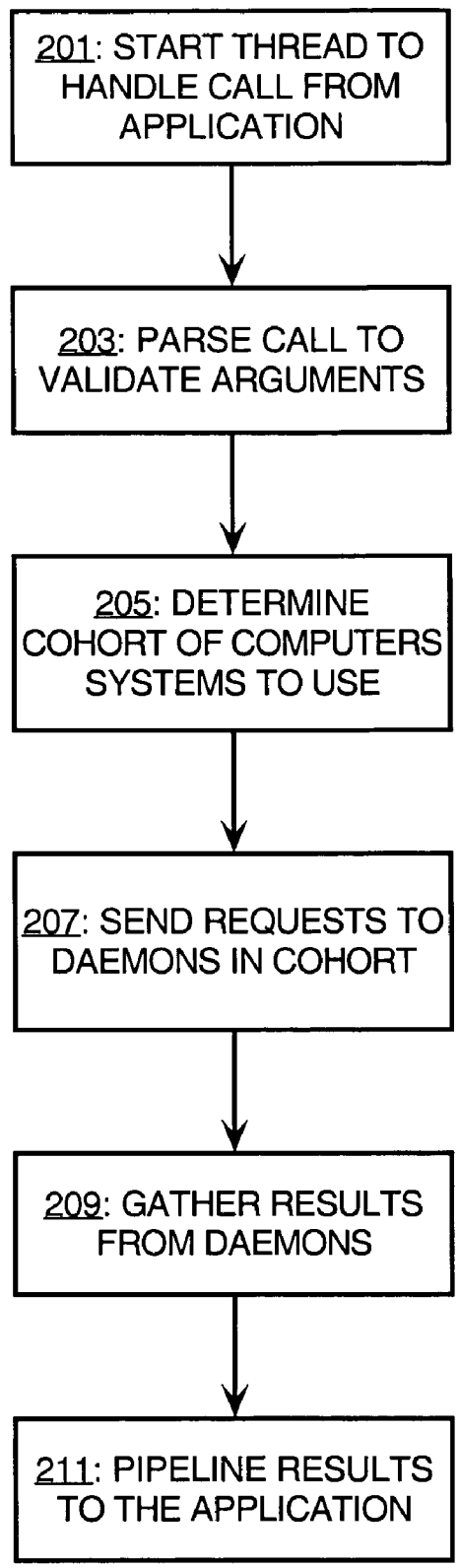
FIG. 2 is a flowchart illustrating the operation of one embodiment of the present invention.

The operation of one embodiment of the invention for coordinating a complex computation across multiple heterogeneous systems is illustrated in FIG. 2. At step 201, the database server 107 receives a query or database statement that includes a call to an external routine listed in the programming registry interface and spawns a thread to handle the call in the statement. An exemplary query in the Structured Query Language (SQL) may be as follows:

```
SELECT   citation_name
FROM     citations c, TABLE(dna_match("ACGTAT")) st
WHERE    st.sequence_id = c.seq_id;
```

This statement is a query that requests a set of citation names (i.e., column "citation_name") by performing a join operation on two sources: a table "st" formed from the results of executing the external function "dna_match" across computer systems in the heterogeneous environment and a citations table "c". The "dna_match" external function is a program 117 that can be executed on various computer systems 103 that accesses a database of genetic sequences in a genome database 119 and returns a sequence identifier ("sequence_id") for all DNA sequences in the genome database 119 that matches the subsequence of nucleotides of the argument within an edit-distance. The nucleotides are adenine (A), guanine (G), thymine (T), and cytosine (C) for DNA and adenine (A), guanine (G), uracil (U), and cytosine (C) for RNA. In this example, the heterogeneous environment 100 includes heterogeneous computer systems 103 and 105 having various proprietary databases of the genetic sequences each having to contend with different databases and interfaces. The citations table "c" correlates the sequence identifiers ("sequence_id"="seq_id"), which are opaque to most users, with more user-understandable source citations of the matched sequences. The desired degree of parallelism can be left blank in query, as shown above, in which case the degree of parallelism may default to the degree already set up in the programming interface registry 111.

At step 203, the call is parsed to verify that the arguments for the external routine are correct in terms of number, type and position. This validation can be performed by accessing a function signature stored in the programming interface registry 111, which specifies the number of arguments that are passed to the external routine and the type of each parameter at each position. For example, the function signature of the "dna_match" function stored in the programming interface registry 111 can, in one representation, be given as:
FUNCTION dna_match(String pattern) RETURN SEQUENCE_ID_SET;

In this signature, "dna_match" is an external function that takes exactly one argument, called "pattern," with the type of "String". The "dna_match" is specified to return a set of sequence identifiers, which is presented as a one-column table. If the arguments are not correct (for example, two arguments are passed to "dna_match" or a number is passed to "dna_match"), the invocation is not validated and an error is returned to the calling application.

Upon passing validation, execution proceeds to step 205 where a "cohort" of computers 101, 103, and 105 (referred to as "nodes") and the threads are determined for ultimately executing the external call to perform the complex calculation specified in the call. There are various ways of determining this cohort without departing from the present invention. In one embodiment, the cohort is determined to be the smallest number of computers subject to (a) the degree of parallelism requested (either specified in parameter to the stub function 113 or defaulted from the registry), (b) whether the foreign database 119 at the node can service the request, (c) the availability of threads in the thread pool for each node, with which those a higher number of available threads being preferred to those with a lower number of available threads, and (d) which node was included earlier, so as to improve locality.

At step 207, the thread executing the stub program 113 makes requests to execute the program 117 on the cohort members, with each computer in the cohort preferably supporting as many parallel threads as possible, given the already executing workload, e.g., up to the available threads. These requests are made to the daemon 115 on each computer in the cohort. If the program 117 referenced in the stub does not require restarting for each request, the request need only pass a fresh set of arguments.

After sending the requests, the thread waits for an acknowledgement that the request was received by each target daemon 115. If a request times out, as defined by the time-out interval in the programming interface registry 111, the request is retried for the number of times specified in the programming interface registry 111. If there is no success after the retries and a partial result is not allowed (also governed by a value in the programming interface registry 111), execution of the call is aborted and control is returned to the application. In case the call is aborted, terminate program requests are sent to the daemons 115 for those cohort computers successfully reached.

If all daemons 115 receive the request successfully, or if there are enough of the daemons to generate a partial result, the thread waits, in step 209, to gather results from all the nodes that received the request. If a node's heartbeat fails (as specified in the programming interface registry 111), the thread stops waiting for results from that node. If partial results are allowed and still obtainable (i.e., there remain computers that can still return valid results), the thread continues to wait. Otherwise, the remaining requests are aborted and control returns to the application.

Finally, at step 211, when all requests on which the thread has been waiting have returned results, the results are processed into the format specified in the stub and returned to the application. In one implementation, the results, one row at a time, are pipelined to the application.

One-to-one Mapping between Nodes and Containers

The approach illustrated with respect to FIG. 2 is powerful and flexible and can handle a variety of different calling strategies. For example, one of the simplest cases is an environment in which there is a one-to-one mapping between nodes and the data for each function that is external to the relational database 109. In other words, each node 103 and 105 is registered with programming interface registry 111 as being capable of executing a function that is coded to access a particular body of data or data container at a particular location within the file systems (e.g. via configuration files when the threads are initialized). In this case, the stub function 113 sends a command to the daemon 115 in all nodes registered to execute the function with the arguments supplied in the SQL query. For concreteness, the function to be executed in parallel on the compute cluster is a function that searches for a given pattern and returns as rows a set of sequence numbers that contains the pattern within a pre-defined edit-distance:

FUNCTION dna_match(String pattern) RETURN SEQUENCE_ID_SET;

To determine all the citations for sequences that contain the pattern "ACGTAT," the user, in this example, issues the following query to the database server 107 as:

```
SELECT   citation_name
FROM     citations c, TABLE(dna_match("ACGTAT")) st
WHERE    st.sequence_id = c.seq_id;
```

In response, the database server 103 calls the stub 113, which issues a remote procedure call (RPC), with "ACG-TAT" as a parameter, to all nodes that have registered for the "dna_match function" in the programming interface registry 111. The respective implementations of the "dna_match" function of the calculation programs 117 are responsible for locating the sequences within their file systems 119 and returning the sequence identifiers to be joined with the citations table.

Non-bijective Mapping between Nodes and Data Containers

The previous case featured a one-to-one or bijective mapping between nodes and data containers; however, an embodiment can support non-bijective or "m-to-n" mappings between "m" nodes and "n" data containers. Non-bijective mappings can be possible if some nodes share access to at least some of the same data containers, for example, through NFS (Network File Sharing). In this situation, an additional implicit parameter is passed to each thread executing a calculation program 117 to indicate the data container that the thread needs to process. The database server 107 need not be able to interpret the structure of the data container, the database server 107 needs to know how to specify the data container (e.g. by a pathname in the file system 119) and how to map the nodes to the containers for each function. Such a mapping table may be stored in the programming registry 111, relational database 109, or elsewhere as shown in TABLE 1:

TABLE 1

| FUNCTION NAME | NODE NAME | DATA CONTAINER |
|---|---|---|
| dna_match | D1sun1 | X:/disk01/sequence.dat |
| dna_match | D1sun1 | X:/disk02/sequence.dat |
| dna_match | D1sun2 | X:/disk01/sequence.dat |
| dna_match | D1sun3 | X:/disk02/sequence.dat |
| protein_match | D1sun1 | Y:/disk01/sequence.dat |
| protein_match | D1sun1 | Y:/disk02/sequence.dat |
| protein_match | D1sun2 | Y:/disk01/sequence.dat |
| protein_match | D1sun2 | Y:/disk02/sequence.dat |

Each row of the mapping in TABLE 1, associates an external function (e.g. "dna_match" or "protein_match") with a node that can execute the external function (e.g. D1sun1, D1sun2, or D1sun3) and the data container that the node can handle. Thus, node D1sun1 can handle invocations of "dna_match" for two different containers and "protein_match" for another two different containers, while D1sun1 only handles one function for one data container ("dna_match" on X:/disk02/sequence.dat). When the external function, for example "dna_match," is invoked, the set of data containers that need to be processed is determined (e.g. X:/disk01/sequence.dat, X:/disk02/sequence.dat), and the nodes assigned to the data container are selected for the cohort based on such criteria as the load on a node, desired degree of parallelism, cache locality (it would be desirable to execute the same function several times on the same node so that the thread could reuse any data that it may have cached), etc.

Attribute-Based Pruning

At this point, the database server 107 has not "pruned" the data containers when executing a function, i.e., reduced the number of data containers that actually need to be searched to satisfy the request. It is possible that some containers need not be accessed for answering a query, so avoiding an expensive search or other operation on the data container is desirable. In this example, the pruning can be done by the implementer of the external function itself. For example, an argument to the external function can be used to determine quickly (i.e., O(1) time) that a certain data container will return no rows by looking at a file header. For example, if a dna_match is desired only on sequences of E. coli, then the E. coli argument can be specified in the query as follows:

```
SELECT   citation_name
FROM     citations c, TABLE(dna_match("ACGTAT", "E.coli")) st
WHERE    st.sequence_id = c.seq_id;
```

Assuming the setup given in TABLE 1, the "dna_match" function on node D1sun1 may be invoked as dna_match (Context, "x:/disk01/sequence.dat", "ACGTAT", "E. coli"); and the "dna_match" function returns quickly if the header of the "x:/disk01/sequence.dat" file for the data container indicates that none of the sequences are for E. coli. However, it may be preferable for the database server 107 to filter out data containers even before transmitting a command to the daemons 115 for invoking the function on the nodes. One solution is to associate each data container with some user-defined attribute that the database server 107 can use to filter out containers depending on the SQL query. For example, this function to container mapping can use an added attribute called "sequence_type" as shown in TABLE 2:

TABLE 2

| DATA CONTAINER | ATTRIBUTE NAME | ATTRIBUTE TYPE | VALUE |
|---|---|---|---|
| X:/disk01/sequence.dat | sequence_type | String | E. coli |
| X:/disk02/sequence.dat | sequence_type | String | Mouse |
| X:/disk01/sequence.dat | sequence_date | Date | Feb. 20, 1997 |
| X:/disk02/sequence.dat | sequence_date | Date | Feb. 06, 1995 |

In this example, the containers can be pruned by an additional predicate in the WHERE clause of the following query:

```
SELECT   citation_name
FROM     citations c, TABLE(dna_match("ACGTAT")) st
WHERE    st.sequence_id = c.seq_id and st.sequence_type = "E.coli"
         and st.sequence_date > 01/01/1996;
```

With this filtering mechanism, all SQL operators can be supported depending on the attribute type.

Parametric Filtering

It is conceivable that the attribute-level filtering mechanism is not sufficiently flexible. In those cases, a user-defined partitioning function can be associated with each function. This function is invoked before calling the daemons 115 to determine the set of data containers that need to be accessed to answer the query. The partitioning function executes within the context of the database server 107 itself and need not be parallelized. The signature of the partitioning function is identical to the function to be executed except that it returns a set of containers. E.g.,

```
PARTITION_FUNCTION dna_match_partition(String pattern,
        String[ ] attribute_names IN,
        String[ ] attribute_values IN,
        String[ ] containers OUT);
```

The first list of parameters is the same as the parameters to the function itself (in this specific example, there is only one parameter, "pattern"), the attribute names and values are passed in by the database server 107 depending on the values specified in the WHERE clause. The user-supplied "dna_match_partition" function uses the attribute names and attribute values to populate the containers as the OUT parameter, which are then used by the stub program 113 to determine the cohort and invoke the respective daemons 115.

WHERE Clause Conditions

It may even be desirable to pass WHERE clause conditions in addition to those needed for data container pruning to the parallel function. For example, the user may wish to supply an "edit distance" in the SQL WHERE condition. This WHERE clause is not used for pruning the containers but is passed to the parallel function to be used when filtering the result set or during the execution itself. Thus, to restrict the search to an edit_distance that is recorded in another table, the following query can be used:

```
SELECT   citation_name
FROM     citations c, TABLE(dna_match("ACGTAT")) st
WHERE    st.sequence_id = c.seq_id and st.sequence_type = "E.coli"
         and st.sequence_date > 01/01/1996 and
         st.edit_distance < (SELECT max(edit_distance) from
         results);
```

The "sequence_type" and "sequence_date" are data container pruning conditions as explained in the parametric pruning case above and are not passed to the parallel external functions. The "edit_distance" condition, on the other hand, is passed to the external function as an implicit WHERE clause context. Preferably, these WHERE clause conditions are restricted to scalar data types; otherwise, the database server 107 may need to pipeline the WHERE clause criterion to the external functions if the WHERE clause is involved in a join with another row source, significantly complicating the implementation of the parallel, external function. Furthermore, the WHERE clause context is passed to the parallel, external function only if the external function returns a set of rows as a table function in the FROM clause.

Multiple Threads in a Physical Node

The partitioning methods discussed above can be easily extended to accommodate multiple threads in a physical node. If a physical node is capable of executing up to N threads for a given function, the node can be treated as N logical nodes or virtual processors when partitioning the work among the threads. Since there is either no intra-cohort communication (i.e. communication between leaf-level threads executing a function) or no intra-cohort communication outside database control, the database server 107 need not attempt to collocate threads on the same physical node. The selection of threads and nodes is based on other parameters discussed above such as access to the data container, load on the physical node, etc.

Hardware Overview

Figure 3:
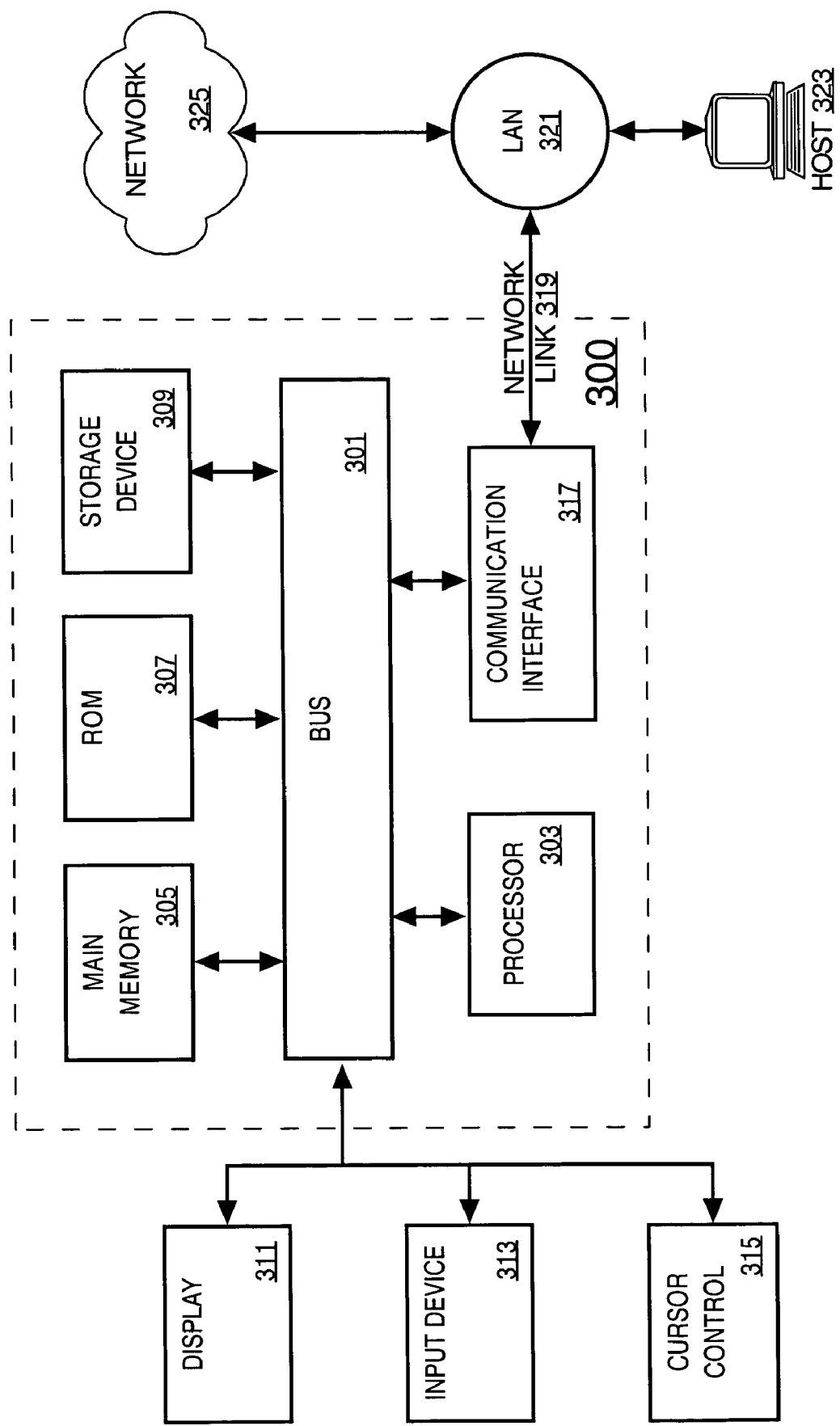
FIG. 3 depicts a computer system that can be used to implement an embodiment of the present invention.

FIG. 3 illustrates a computer system 300 upon which an embodiment according to the present invention can be implemented. The computer system 300 includes a bus 301 or other communication mechanism for communicating information and a processor 303 coupled to the bus 301 for processing information. The computer system 300 also includes main memory 305, such as a random access memory (RAM) or other dynamic storage device, coupled to the bus 301 for storing information and instructions to be executed by the processor 303. Main memory 305 can also be used for storing temporary variables or other intermediate information during execution of instructions by the processor 303. The computer system 300 may further include a read only memory (ROM) 307 or other static storage device coupled to the bus 301 for storing static information and instructions for the processor 303. A storage device 309, such as a magnetic disk or optical disk, is coupled to the bus 301 for persistently storing information and instructions.

The computer system 300 may be coupled via the bus 301 to a display 311, such as a cathode ray tube (CRT), liquid crystal display, active matrix display, or plasma display, for displaying information to a computer user. An input device 313, such as a keyboard including alphanumeric and other keys, is coupled to the bus 301 for communicating information and command selections to the processor 303. Another type of user input device is a cursor control 315, such as a mouse, a trackball, or cursor direction keys, for communicating direction information and command selections to the processor 303 and for controlling cursor movement on the display 311.

According to one embodiment of the invention, coordination of complex calculations across multiple nodes is provided by the computer system 300 in response to the processor 303 executing an arrangement of instructions contained in main memory 305. Such instructions can be read into main memory 305 from another computer-readable medium, such as the storage device 309. Execution of the arrangement of instructions contained in main memory 305 causes the processor 303 to perform the process steps described herein. One or more processors in a multi-processing arrangement may also be employed to execute the instructions contained in main memory 305. In alternative embodiments, hard-wired circuitry may be used in place of or in combination with software instructions to implement the embodiment of the present invention. In another example, reconfigurable hardware such as Field Programmable Gate Arrays (FPGAs) can be used, in which the functionality and connection topology of its logic gates are customizable at run-time, typically by programming memory look up tables. Thus, embodiments of the present invention are not limited to any specific combination of hardware circuitry and software.

The computer system 300 also includes a communication interface 317 coupled to bus 301. The communication interface 317 provides a two-way data communication coupling to a network link 319 connected to a local network 321. For example, the communication interface 317 may be a digital subscriber line (DSL) card or modem, an integrated services digital network (ISDN) card, a cable modem, a telephone modem, or any other communication interface to provide a data communication connection to a corresponding type of communication line. As another example, communication interface 317 may be a local area network (LAN) card (e.g. for Ethernet™ or an Asynchronous Transfer Model (ATM) network) to provide a data communication connection to a compatible LAN. Wireless links can also be implemented. In any such implementation, communication interface 317 sends and receives electrical, electromagnetic, or optical signals that carry digital data streams representing various types of information. Further, the communication interface 317 can include peripheral interface devices, such as a Universal Serial Bus (USB) interface, a PCMCIA (Personal Computer Memory Card International Association) interface, etc. Although a single communication interface 317 is depicted in FIG. 3, multiple communication interfaces can also be employed.

The network link 319 typically provides data communication through one or more networks to other data devices. For example, the network link 319 may provide a connection through local network 321 to a host computer 323, which has connectivity to a network 325 (e.g. a wide area network (WAN) or the global packet data communication network now commonly referred to as the "Internet") or to data equipment operated by a service provider. The local network 321 and the network 325 both use electrical, electromagnetic, or optical signals to convey information and instructions. The signals through the various networks and the signals on the network link 319 and through the communication interface 317, which communicate digital data with the computer system 300, are exemplary forms of carrier waves bearing the information and instructions.

The computer system 300 can send messages and receive data, including program code, through the network(s), the network link 319, and the communication interface 317. In the Internet example, a server (not shown) might transmit requested code belonging to an application program for implementing an embodiment of the present invention through the network 325, the local network 321 and the communication interface 317. The processor 303 may execute the transmitted code while being received and/or store the code in the storage device 309, or other non-volatile storage for later execution. In this manner, the computer system 300 may obtain application code in the form of a carrier wave.

The term "computer-readable medium" as used herein refers to any medium that participates in providing instructions to the processor 305 for execution. Such a medium may take many forms, including but not limited to non-volatile media, volatile media, and transmission media. Non-volatile media include, for example, optical or magnetic disks, such as the storage device 309. Volatile media include dynamic memory, such as main memory 305. Transmission media include coaxial cables, copper wire and fiber optics, including the wires that comprise the bus 301. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the present invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While the present invention has been described in connection with a number of embodiments and implementations, the present invention is not so limited but covers various obvious modifications and equivalent arrangements, which fall within the purview of the appended claims.

What is claimed is:

1. A method comprising performing a machine-executed operation involving instructions, wherein the machine-executed operation is at least one of:
   A) sending said instructions over transmission media;
   B) receiving said instructions over transmission media;
   C) storing said instructions onto a machine-readable storage medium; and
   D) executing the instructions;
   wherein said instructions are instructions which, when executed by one or more processors, cause the one or more processors to perform the steps of:
      at each node of a plurality of nodes, executing a corresponding process; and
      at a database system, receiving a statement specifying an external routine for performing a computation and, in response to receiving the statement:
      concurrently transmitting a plurality of commands for performing the computation to each said corresponding process;
      receiving results from each said corresponding process; and completing processing of the statement based on the results received from each said corresponding process.

2. The method of claim 1, wherein the steps of concurrently transmitting, receiving results, and completing processing are performed by said database system.

3. The method of claim 1, wherein at least one of said plurality of nodes is implemented using a different type of hardware, operation system software, or application software than said database system.

4. The method of claim 1, wherein the corresponding process, executed on each node of said plurality of nodes, is configured to start a program to perform the computation in response to a command received from said database system.

5. The method of claim 1, wherein each said corresponding process instructs a program to perform the computation upon a data container.

6. A method comprising performing a machine-executed operation involving instructions, wherein the machine-executed operation is at least one of:
   A) sending said instructions over transmission media;
   B) receiving said instructions over transmission media;
   C) storing said instructions onto a machine-readable storage medium; and
   D) executing the instructions;
   wherein said instructions are instructions which, when executed by one or more processors, cause the one or more processors to perform the steps of:
      receiving a statement, at a database system, specifying an external routine for performing the computation; and
      in response to receiving the statement:
         transmitting a plurality of commands for performing the computation to a plurality of respective processes;
         receiving results from each said corresponding process; and
         completing processing of the statement based on the results received from each said corresponding process.

7. A method according to claim 6, wherein said instructions, when executed by the one or more processors, further cause the one or more processors to perform the step of:
   determining a cohort of nodes from among a plurality of nodes capable of performing the computation,
   wherein the plurality of the respective processes correspond to the cohort of the nodes.

8. A method according to claim 7, wherein the plurality of nodes includes at least one node not included in the cohort of the nodes.

9. A method according to claim 7, wherein said determining is based on a degree of parallelism supported by each of the nodes.

10. A method according to claim 7, wherein said instructions, when executed by the one or more processors, further cause the one or more processors to perform the step of accessing a registry specifying an association between the programs and the data containers, wherein said determining is based on the association between the programs and the data containers.

11. A method according to claim 7, wherein said instructions, when executed by the one or more processors, further cause the one or more processors to perform the step of accessing a registry specifying respective attributes for the data containers, wherein said determining is based on matching the respective attributes for the data containers with a parameter in the statement.

12. A method according to claim 7, wherein said instructions, when executed by the one or more processors, further cause the one or more processors to perform the step of accessing a registry specifying a partitioning function associated with the programs and the data containers, wherein said determining is based on the results from executing the partitioning function associated with the programs and the data containers.

13. The method of claim 6, wherein the steps of transmitting the plurality of commands, receiving results, and completing processing are performed by said database system.

14. The method of claim 6, wherein each of the plurality of respective processes is executing on one of a plurality of nodes, and wherein at least one of said plurality of nodes is implemented using a different type of hardware, operation system software, or application software than said database system.

15. The method of claim 6, wherein each of the respective processes is configured to start a program to perform the computation in response to said commands.

16. A method according to claim 15, wherein at least some of the programs, started by each of the respective processes, execute in parallel.

17. The method of claim 6, wherein each said corresponding process instructs a program to perform the computation upon a data container.

* * * * *